US012741159B2

(12) United States Patent
Carlsson

(10) Patent No.: US 12,741,159 B2
(45) Date of Patent: Sep. 22, 2026

(54) RADIOTHERAPY APPARATUS AND METHOD FOR DELIVERING RADIATION TO A SUBJECT

(71) Applicant: Elekta Limited, Crawley (GB)

(72) Inventor: Per Carlsson, Crawley (GB)

(73) Assignee: Elekta Limited, Crawley (GB)

( * ) Notice: Subject to any disclaimer, the term of this patent is extended or adjusted under 35 U.S.C. 154(b) by 172 days.

(21) Appl. No.: 18/711,084

(22) PCT Filed: Nov. 18, 2022

(86) PCT No.: PCT/EP2022/082509
§ 371 (c)(1),
(2) Date: May 16, 2024

(87) PCT Pub. No.: WO2023/089145
PCT Pub. Date: May 25, 2023

(65) Prior Publication Data

US 2025/0235719 A1 Jul. 24, 2025

(30) Foreign Application Priority Data

Nov. 18, 2021 (GB) ..................................... 2116673

(51) Int. Cl.
*A61N 5/00* (2006.01)
*A61N 5/10* (2006.01)

(52) U.S. Cl.
CPC ......... *A61N 5/1067* (2013.01); *A61N 5/1049* (2013.01); *A61N 5/107* (2013.01); *A61N 5/1081* (2013.01)

(58) Field of Classification Search
CPC .......... A61N 2005/1061; A61N 5/1049; A61N 5/1067; A61N 5/107; A61N 5/1081
See application file for complete search history.

(56) References Cited

U.S. PATENT DOCUMENTS

2017/0128750 A1* 5/2017 Filiberti ............... A61N 5/1069

FOREIGN PATENT DOCUMENTS

| | | | |
|---|---|---|---|
| GB | 2594489 | A | 11/2021 |
| WO | WO-2019160958 | A1 | 8/2019 |
| WO | WO-2020150505 | A1 | 7/2020 |

OTHER PUBLICATIONS

"British Application Serial No. 2116673.1, Examination Report dated May 13, 2022", (May 13, 2022), 6 pgs.
"International Application Serial No. PCT/EP2022/082509, International Search Report dated Mar. 2, 2023", (Mar. 2, 2023), 4 pgs.
"International Application Serial No. PCT/EP2022/082509, Written Opinion dated 03-02- 2023", (Mar. 2, 2023), 8 pgs.

* cited by examiner

*Primary Examiner* — Dani Fox
(74) *Attorney, Agent, or Firm* — Schwegman Lundberg & Woessner, P.A.

(57) ABSTRACT

Disclosed herein is a radiotherapy apparatus comprising a radiation source coupled to a rotatable gantry, a movable subject support surface and a controller. The controller is configured to obtain a first and a second anatomical location of the patient, determine a vector using the first and second anatomical location, apply radiation from the radiation source to the first and second anatomical location and move the subject support surface to the gantry based on the angular deviation.

27 Claims, 9 Drawing Sheets

RADIOTHERAPY APPARATUS AND METHOD FOR DELIVERING RADIATION TO A SUBJECT

PRIORITY APPLICATIONS

Figure 1A:
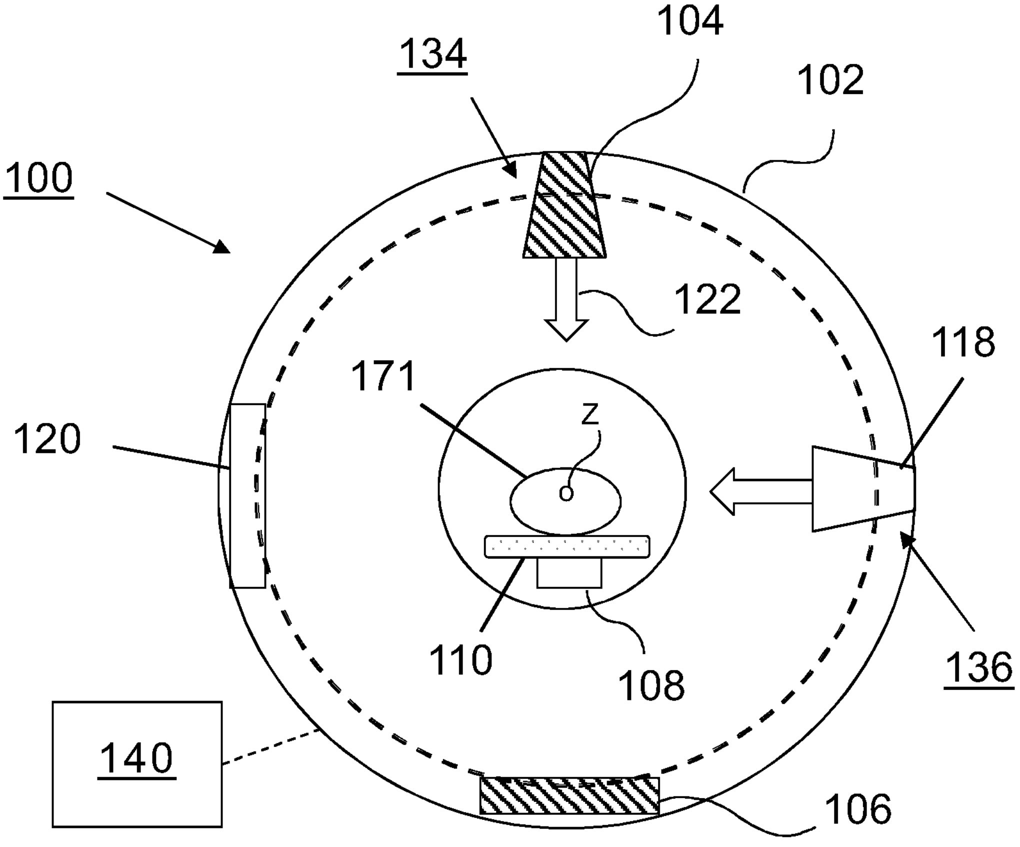

This application is a U.S. National Stage Filing under 35 U.S.C. § 371 from International Application No. PCT/EP2022/082509, filed on Nov. 18, 2022, and published as WO2023/089145 on May 25, 2023, which claims the benefit of priority to British Application No. 2116673.1, filed on Nov. 18, 2021; the benefit of priority of each of which is hereby claimed herein, and which applications and publication are hereby incorporated herein by reference in their entireties.

This disclosure relates generally to a radiotherapy apparatus, and in particular to a radiotherapy apparatus with a movable subject support surface.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

There exist a variety of treatments which are suited to the treatment of elongate target regions, for example lesions along the spine. Such treatments include helical treatment, where a patient is moved along the gantry's rotation axis as the beam generation system is rotated by the gantry, such that the radiation beam sweeps out a helical shape from the patient's perspective and an elongate target region of the patient can be treated.

Typically, prior to receiving a radiotherapy treatment, a patient is positioned on a couch such that a radiation target on or within the patient's body is accessible by the beam. This may include, for example, aligning a target with a longitudinal axis of the radiotherapy device. In radiotherapy treatments which involve long, curved and/or separate target regions, it is often difficult to position a patient such that the target region(s) can be provided with the necessary radiation without damaging neighbouring healthy tissue. In some cases, a patient may be positioned in a highly uncomfortable position, and may be required to remain very still in that position for a considerable amount of time.

Moreover, deviations between a patient's position on the couch at the time of treatment and the patient's position during the preparation of a treatment plan can introduce a risk of radiation being delivered to an unintended region, which is undesirable. If treatment is already in progress, such deviations typically require treatment to be halted or paused to correct the patient's position or the treatment delivery plan, which is disruptive and costs time. In cases where there has been an error in the angular set up of a patient, or when multiple target regions are to be treated, current treatments require the patient to be repositioned. However, repeatedly repositioning a patient in this manner can be difficult and time consuming.

The present invention seeks to address these and other issues encountered in the prior art.

SUMMARY

Aspects and features of the present disclosure are described in the accompanying claims.

One aspect of the present disclosure provides a radiotherapy apparatus, comprising a radiation source coupled to a rotatable gantry, a movable subject support surface and a controller. The controller is configured to obtain a first anatomical location L1 of a patient and a second anatomical location L2 of the patient and determine a vector using the first anatomical location L1 and the second anatomical location L2, a directional component of the vector being an angular deviation from a rotational axis of the gantry. The controller is further configured to apply radiation from the radiation source to the first anatomical location L1 at a time T1, move the subject support surface relative to the gantry based on the angular deviation, and apply radiation from the radiation source to the second anatomical location L2 at a time T2.

In some embodiments, the controller may be further configured to obtain the first anatomical location L2 and the second anatomical location L2 by receiving image data and identifying the first anatomical location L1 and the second anatomical location L2 using the received image data.

In some embodiments, the controller may be configured to determine the vector by registering the image data with reference image data, and the angular deviation may be determined based on a difference in alignment between the image data and the reference image data.

In some embodiments, the radiotherapy apparatus may further comprise an imaging system configured to generate image data, and receiving the image data may comprise receiving the image data from the imaging system.

In some embodiments, the controller may be configured to apply radiation to a target region between the first anatomical location L1 and the second anatomical location L2 as the subject support surface is moved.

In some embodiments, the controller may be configured to apply radiation according to a treatment plan.

In some embodiments, the controller may be configured to apply radiation according to a helical treatment in which radiation is applied during movement of the subject support surface and during rotation of the gantry.

The helical treatment may be applied from the first anatomical location L1 to the second anatomical location L2.

In some embodiments, the first anatomical location L1 and the second anatomical location L2 may be locations on a single target.

In some embodiments, the first anatomical location L1 may correspond to a position on a first target, and the second anatomical location L2 may correspond to a position on a second target distinct from the first target.

In some embodiments, the controller may be further configured to obtain a third anatomical location L3 of the patient, determine a second vector using the second anatomical location L2 and the third anatomical location L3, a directional component of the second vector being a second angular deviation from the rotational axis of the gantry. The controller may be further configured to move the subject support surface relative to the gantry based on the second angular deviation and apply radiation from the radiation source to the third anatomical location L3 at a time T3.

In some embodiments, the radiotherapy apparatus may further comprise a beam shaping apparatus configured to shape a beam of radiation. Radiation from the radiation source may be applied as a beam shaped by the beam shaping apparatus, and the controller may be configured to control the beam shaping apparatus to shape the beam in accordance with a treatment plant and/or an alignment of the beam and a target to which radiation is being applied.

In some embodiments, the controller may be configured to move the subject support surface by translating the subject support surface in at least two spatial dimensions.

In some embodiments, the angular deviation may comprise at least one angular error value in at least one dimension.

Another aspect of the present disclosure concerns a method for controlling a radiotherapy apparatus comprising a radiation source coupled to a rotatable gantry and movable subject support surface. The method comprises obtaining a first anatomical location L1 of a patient and a second anatomical location L2 of the patient, determining a vector using the first anatomical location L1 of the patient and the second anatomical location L2 of the patient, a directional component of the vector being an angular deviation from a rotational axis of the gantry, and outputting control instructions. The control instructions are configured to control the radiotherapy apparatus to apply radiation from the radiation source to the first anatomical location L1 at a time T1, move the subject support surface relative to the gantry based on the angular deviation, and apply radiation from the radiation source to the second anatomical location L2 at a time T2.

In some embodiments, obtaining the first anatomical location L1 and the second anatomical location L2 may comprise receiving image data and identifying the first anatomical location L1 and the second anatomical location L2 using the received image data.

In some embodiments, determining the vector may comprise registering the image data with reference image data and determining the angular deviation based on a difference in alignment between the image data and the reference image data.

In some embodiments, receiving the image data may comprise generating the image data using an imaging system of the radiotherapy apparatus and receiving the image data from the imaging system.

In some embodiments, outputting control instructions configured to control the radiotherapy apparatus to move the subject support surface may comprise outputting control instructions configured to control the radiotherapy apparatus to apply radiation to a target region between the first anatomical location L1 and the second anatomical location L2 as the subject support surface is moved.

In some embodiments, the method may further comprise outputting control instructions configured to control the radiotherapy apparatus to apply radiation according to a treatment plan.

In some embodiments, the method may further comprise outputting control instructions configured to control the radiotherapy apparatus to apply radiation according to a helical treatment in which radiation is applied during movement of the subject support surface and during rotation of the gantry.

In some embodiments, outputting control instructions configured to control the radiotherapy apparatus to apply radiation according to a helical treatment may comprise outputting control instructions configured to control the radiotherapy apparatus to apply radiation according to a helical treatment from the first anatomical location L1 to the second anatomical location L2.

In some embodiments, the first anatomical location L1 and the second anatomical location L2 may be locations on a single target.

In some embodiments, the first anatomical location L1 may correspond to a position on a first target, and the second anatomical location L2 may correspond to a position on a second target, distinct from the first target.

In some embodiments, the method may further comprise obtaining a third anatomical location L2 of the patient, determining a second vector using the second anatomical location L2 and the third anatomical location L3, a directional component of the second vector being a second angular deviation from the rotational axis of the gantry, outputting control instructions configured to control the radiotherapy apparatus to move the subject support surface relative to the gantry based on the second angular deviation and apply radiation from the radiation source to the third anatomical location L3 at a time T3.

In some embodiments, the method may further comprise outputting control instructions configured to control the radiotherapy apparatus to apply radiation as a beam shaped by a beam shaping apparatus and to shape the beam in accordance with a treatment plan and/or an alignment of the beam and a target to which the radiation is being applied.

In some embodiments, the method may further comprise outputting control instructions configured to control the radiotherapy apparatus to move the subject support surface by translating the subject support surface in at least two spatial dimensions.

In some embodiments, the angular deviation may comprise at least one angular error value in at least one dimensions.

In another aspect of the present disclosure, a computer-readable medium is provide which comprises instructions that, when executed by one or more processors of a computer device, cause the one or more processors to perform any of the methods disclosed herein.

FIGURES

Figure 1B:
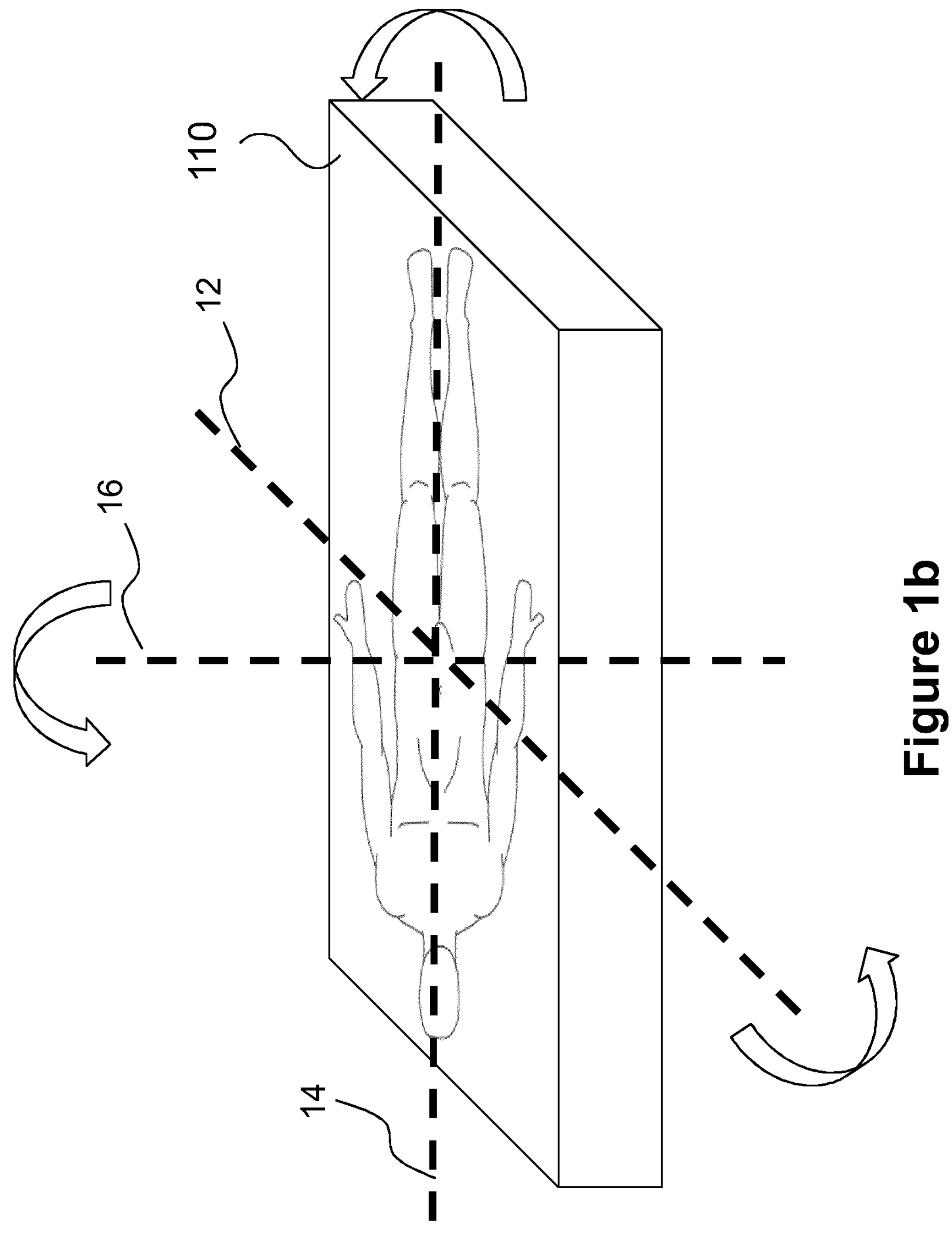
Figure 2A:
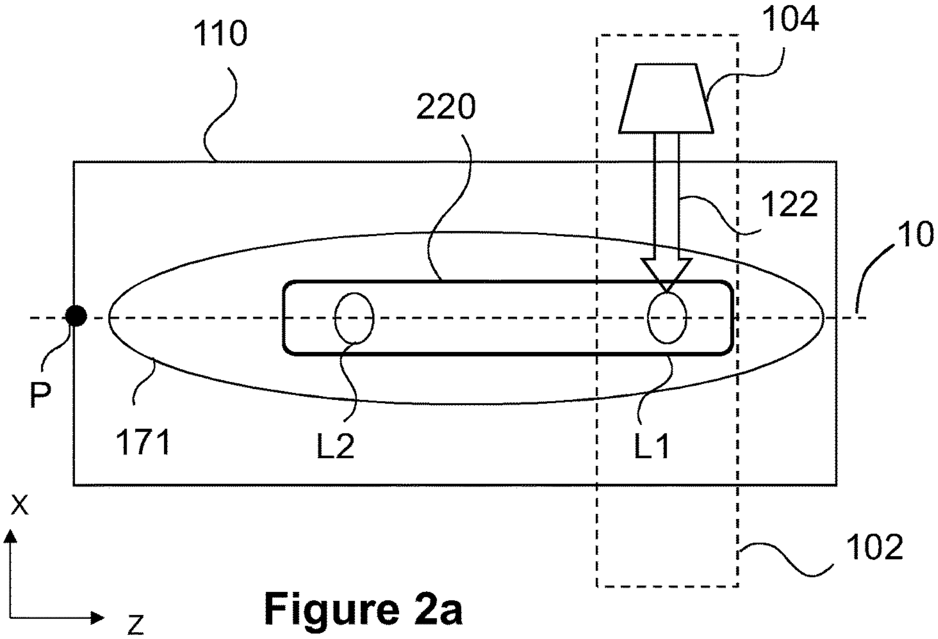
Figure 2B:
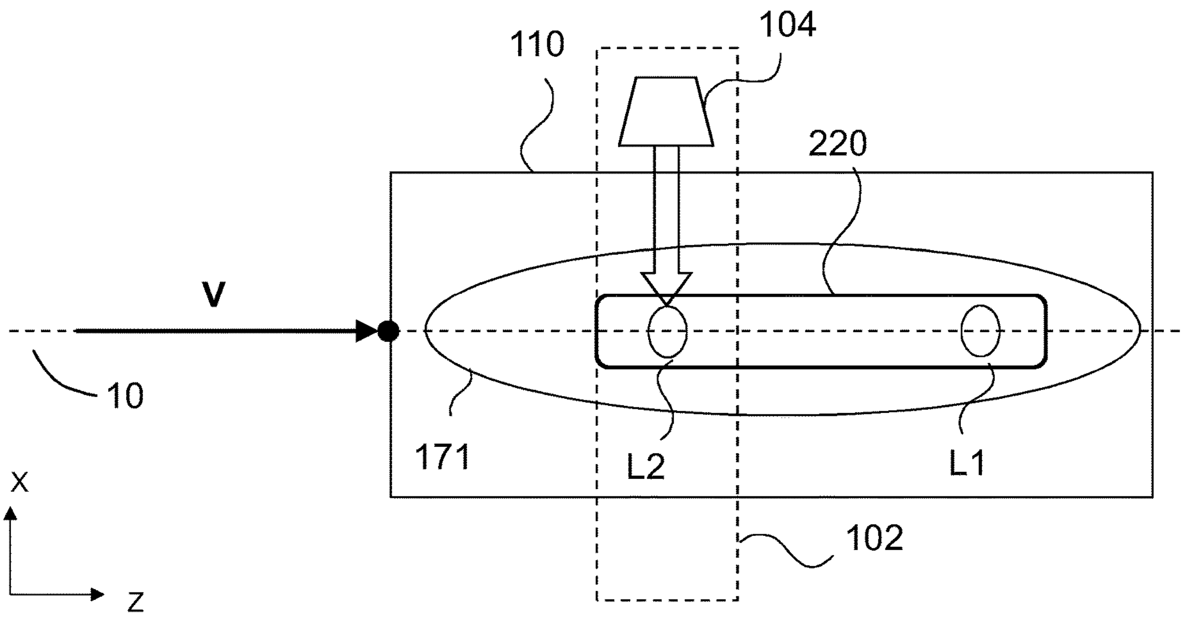
Figure 3A:
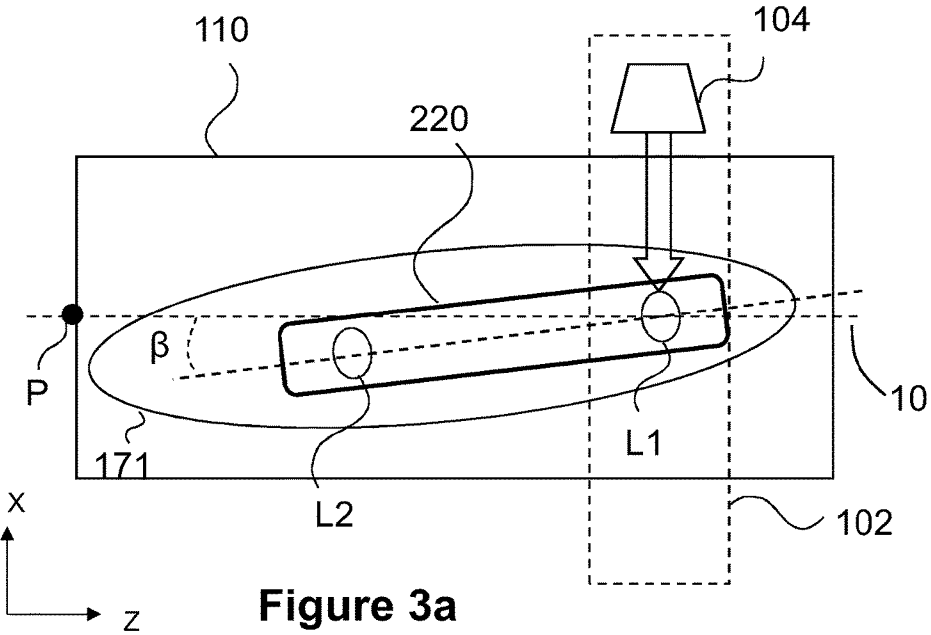
Figure 3B:
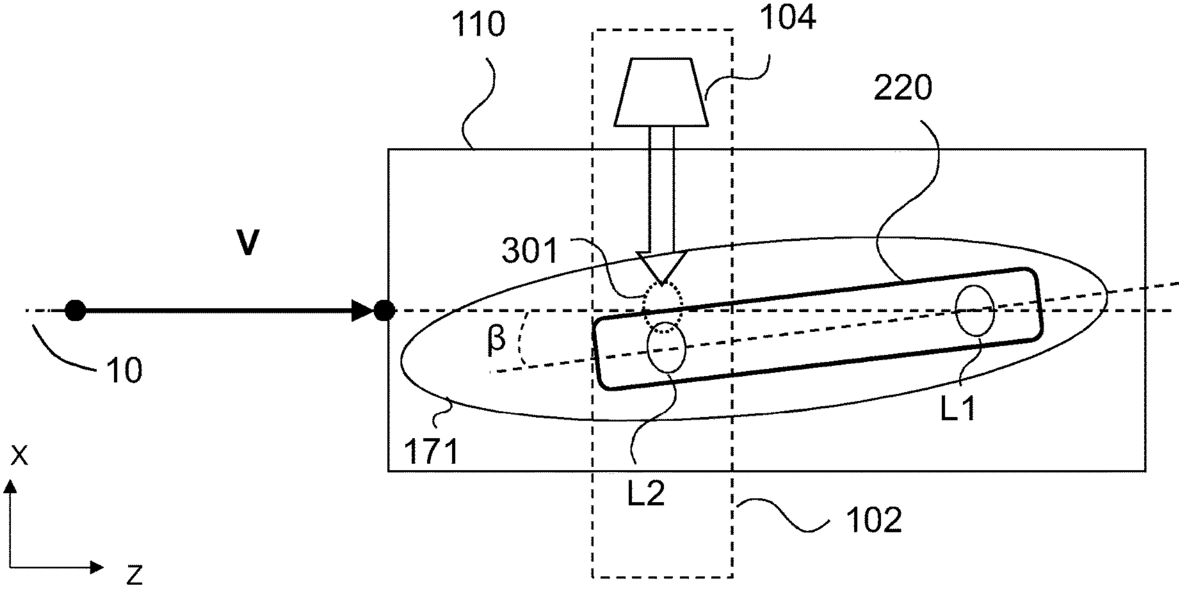
Figure 4A:
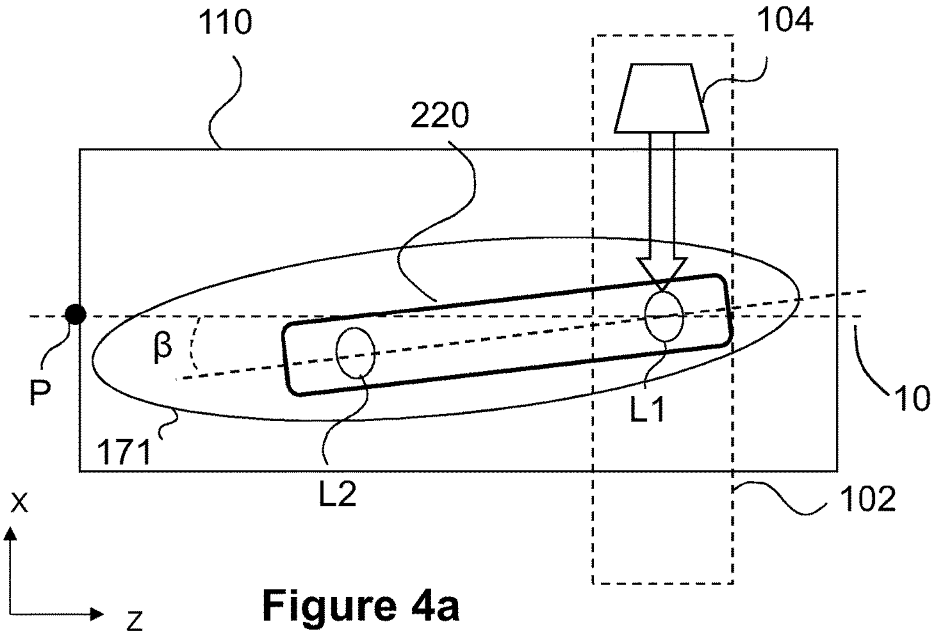
Figure 4B:
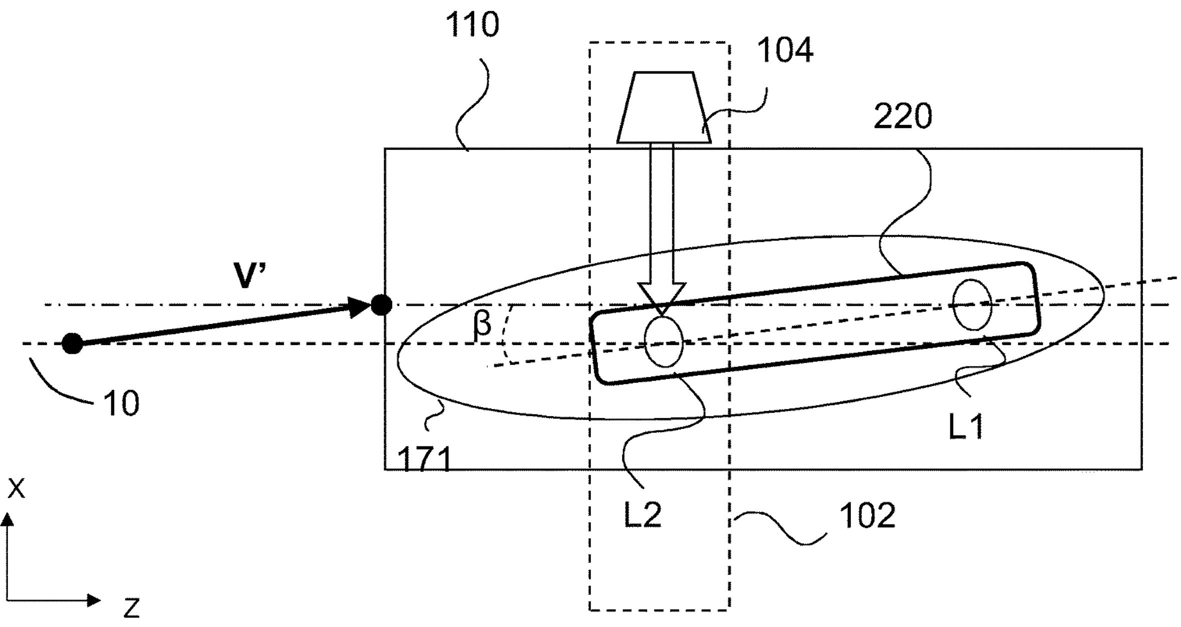
Figure 5A:
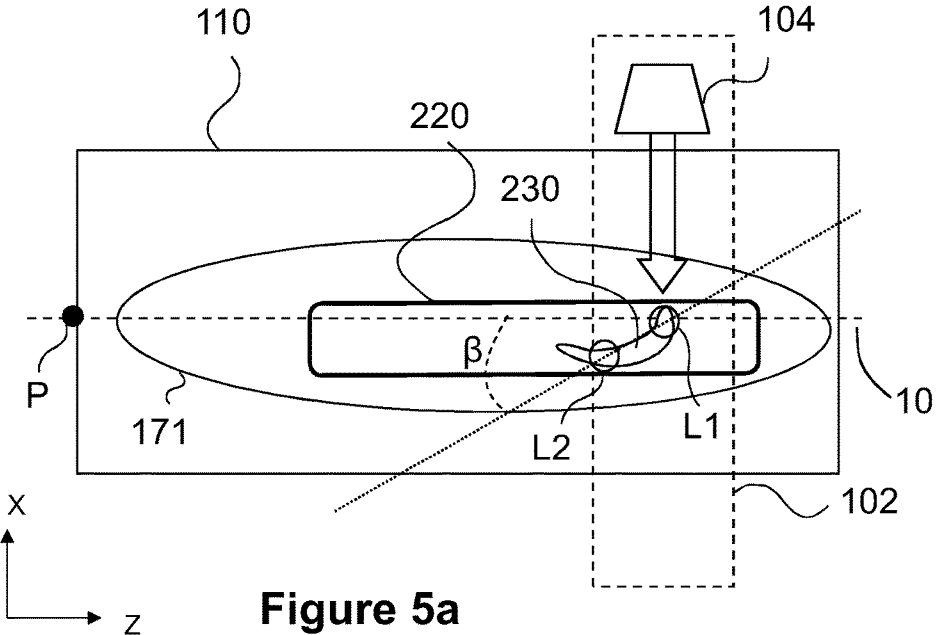
Figure 5B:
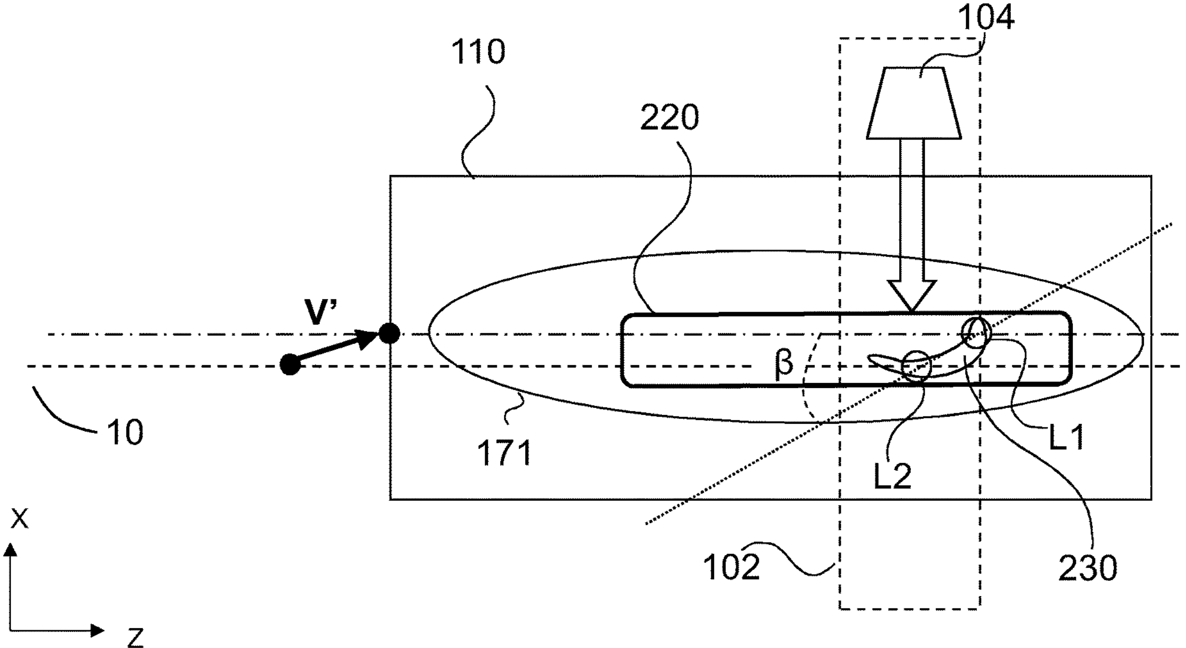
Figure 5C:
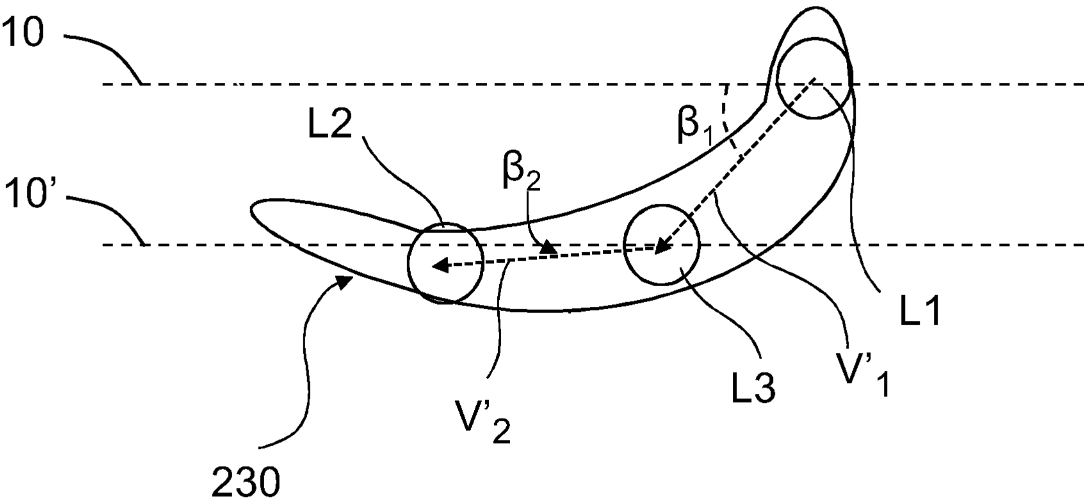
Figure 5D:
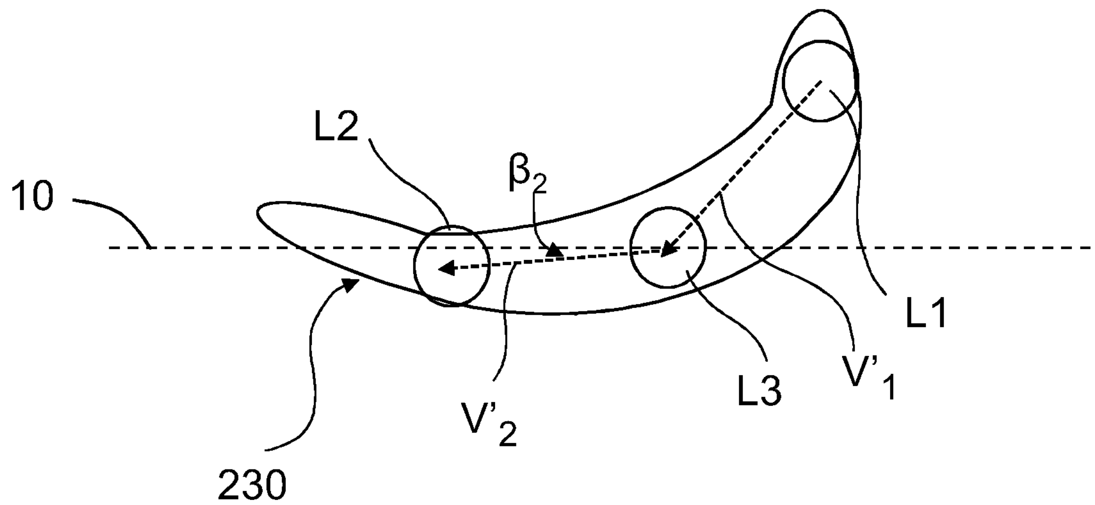
Figure 6:
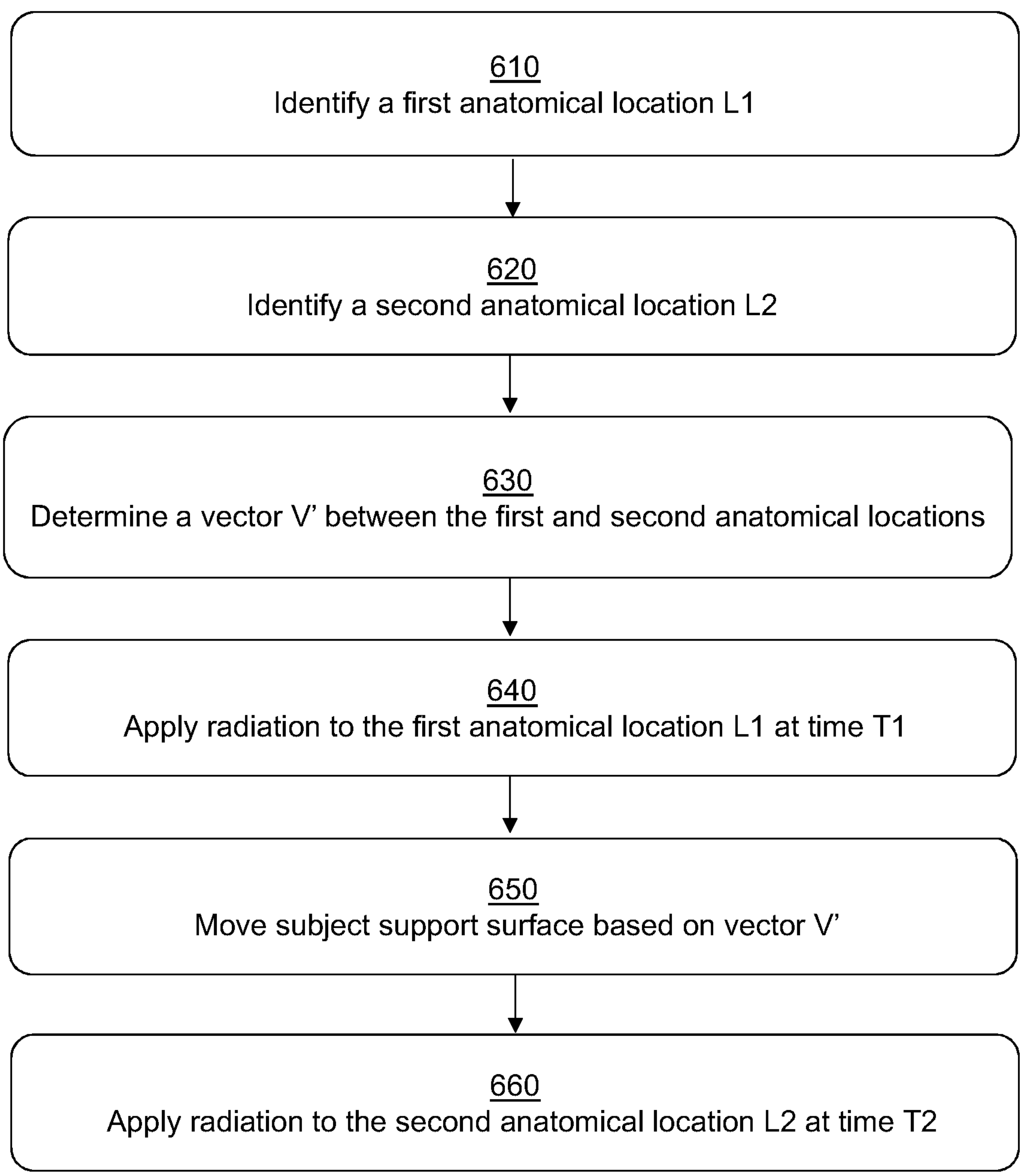
Figure 7:
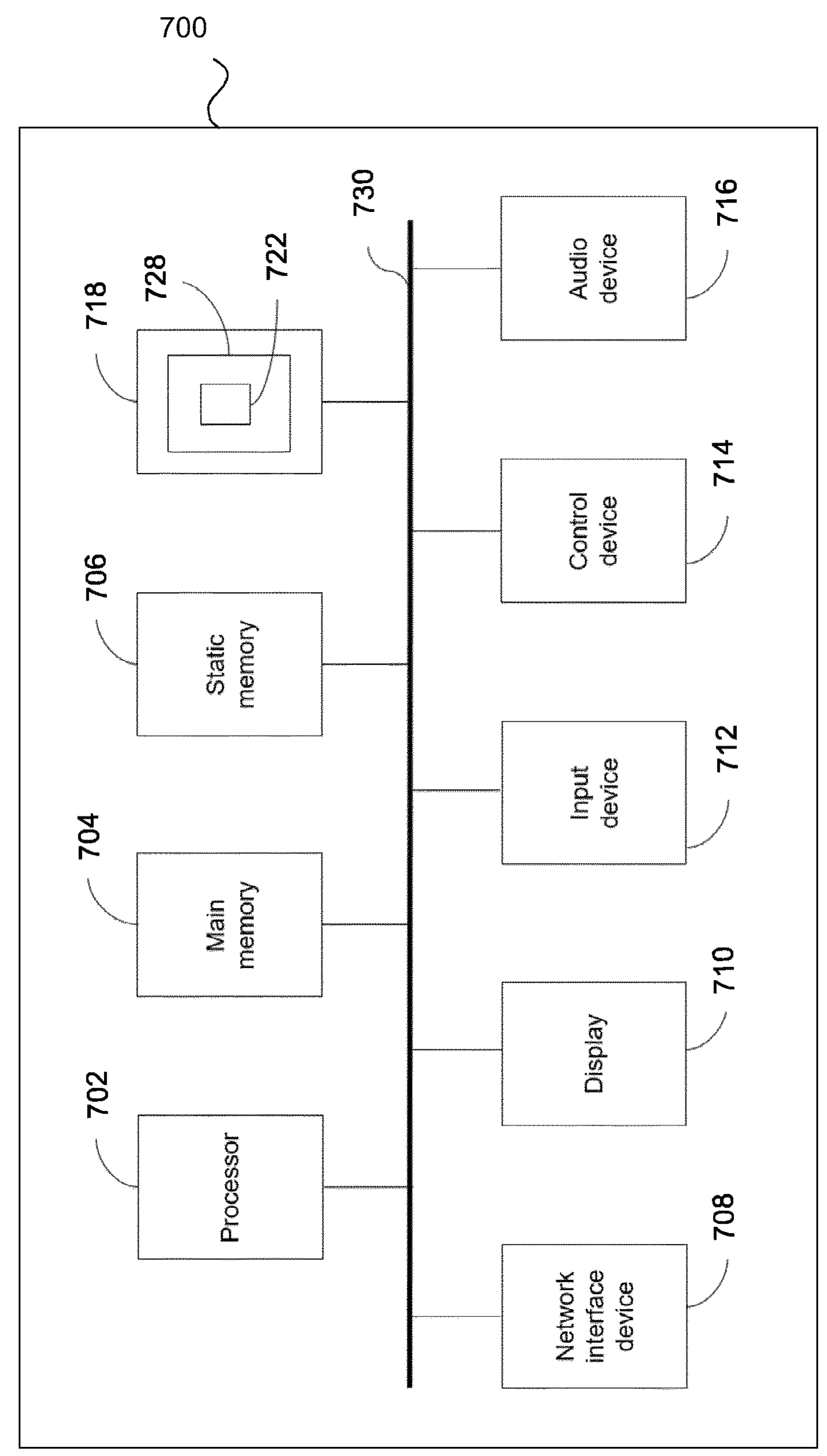

Specific embodiments are now described, by way of example only, with reference to the drawings, in which:

FIG. 1*a* depicts a radiotherapy device or apparatus according to the present disclosure;

FIG. 1*b* depicts a couch for use with a radiotherapy device or apparatus according to the present disclosure;

FIGS. 2*a* and 2*b* show simplified schematic overhead views of the radiation head and the couch according to the present disclosure;

FIGS. 3*a* and 3*b* show simplified schematic overhead views of the radiation head and the couch according to the present disclosure;

FIGS. 4*a* and 4*b* show simplified schematic overhead views of the radiation head and the couch according to the present disclosure;

FIGS. 5*a* and 5*b* show simplified schematic overhead views of the radiation head and the couch according to the present disclosure;

FIGS. 5*c* and 5*d* illustrate a target region with a plurality of anatomical locations according to the present disclosure;

FIG. 6 is a flowchart setting out a method for controlling a radiotherapy apparatus to compensate for an angular deviation of a target region from a longitudinal axis during radiotherapy treatment; and FIG. 7 depicts a block diagram of a computing device.

OVERVIEW

Aspects of the disclosure will be described below. In overview, and without limitation, the present application relates to providing a radiotherapy apparatus which can adjust the positioning of a subject support surface, and hence can adjust the positioning of a patient positioned on the subject support surface, during radiotherapy treatment. For example, this positioning of the subject support surface may be made to compensate for an angular deviation of a radiation target (such as a tumour), such as when a tumour does not align precisely with an intended treatment trajectory. Such a radiotherapy apparatus may be particularly suited for use in the delivery of helical or multi-isocentre radiotherapy treatments, where a small angular deviation can result in dose translation errors. For elongate tumours which have an elongate axis, angular deviations may be caused, for example, by an error in set up, where the tumour's elongate axis is not properly aligned with the apparatus as per the treatment plan. As a further example, an angular deviation may stem from the shape of the target region—an elongate, yet non-linear target region, for example, cannot be easily aligned with a rotational axis of the gantry. Further examples of angular deviations will be described herein.

Such deviations between the target region and the rotational axis, or similarly deviations between the target region and a predetermined positioning of the target region corresponding to a treatment plan, can be especially problematic, for example in applications where elongate areas are being treated. Such elongate areas can be found, for example, in treatments of the spine. A small angular error then causes a greater error in translation of dose as the distance from isocentre increases. For example, an angular error of 1.5 degrees in patient setup when aligning a tumour axis or position with the machine longitudinal axis could mean that, at a distance of 20 cm from the isocentre, there is a dose translation error of 5 mm. Such dose translation errors can result in the treatment being halted or stopped while a patient is repositioned and/or the treatment delivery (e.g. beam shaping, intensity, etc.) is adjusted accordingly, in order to prevent the harm of healthy tissue. Halting or stopping treatment can be time-consuming and uncomfortable for the patient.

Apparatuses and methods described in the present application may be used during radiotherapy treatment to adapt a treatment plan, or as part of a treatment plan, to account for angular deviations of a target region within a patient with respect to a rotational axis of a gantry, thereby avoiding a full reoptimisation or recalculation of the treatment plan. Instead, a controller (such as a processor) can control movement of the subject support surface in such a manner as to compensate for the deviation, so that the treatment can be delivered as planned. In some embodiments, the movement of the subject support surface may be included in a treatment plan. For example, if the shape of the target region is substantially non-linear, e.g. curved, or if a plurality of target regions are to be treated, the subject support surface may be moved from one position to another in order to better align the target region being treated with the isocentre. Such embodiments will be described in detail with reference to FIGS. 4*a*, 4*b*, 5*a* and 5*b*. In some embodiments, the angular deviation may comprise a deviation between the patient position at the time of treatment, and the predetermined patient position corresponding to the treatment plan.

The described apparatus and methods may also allow compensation for deviation (e.g. angular angular) without the need for tilting or pitching the subject support surface, thus allowing for a more accurate treatment delivery and a more comfortable experience for the patient. The need for the subject support surface to be a complex machine may also be eliminated, as there may not be a requirement for the subject support surface to be capable of tilting, pitching, rotating, etc.

The described subject matter may also allow a treatment to be carried out on a patient without having to re-position the patient due to an angular deviation between the patient position at time of treatment and a predetermined patient position corresponding to a treatment plan. This means that there is no need for the patient to be imaged and the position of the patient adjusted, which can be difficult and time consuming. Moreover, the described subject matter may allow a treatment of a plurality of target regions to be carried out, without the need for the patient to be repositioned during treatment.

DETAILED DESCRIPTION

FIG. 1*a* is a view of an exemplary radiotherapy apparatus 100. Radiotherapy apparatus 100 is, for example, an Image Guided Radiotherapy (IGRT) device comprising a linear accelerator (LINAC).

The radiotherapy apparatus 100 includes a gantry 102, which supports a treatment system 134 and an imaging system 136. In this example, the treatment system 134 and the imaging system 136 are attached to the gantry 102, so that they are rotatable with the gantry 102, e.g. so that they rotate as the gantry 102 rotates. Positioned generally along an axis 'Z' central to the gantry is a couch 110 upon which a patient may be positioned for radiotherapy treatment. The couch may also be referred to as a patient or subject positioning system herein. The Z axis may align generally with the axis of rotation of the gantry 102. The couch 110 may be referred to as a table or a subject support surface.

FIG. 1*a* also shows a patient (or subject) 171 positioned on the couch 110 of the radiotherapy apparatus 100. The couch 110 includes one or more actuators 108 which actuate the couch 110 in one or more dimensions. This is illustrated in FIG. 1*b*.

Referring now to FIG. 1*b*, couch 110 is shown with a pitch axis 12, roll axis 14 and yaw axis 16. The radiotherapy apparatus 100 may comprise a rotation mechanism or system, which is configured to tilt the patient support apparatus, e.g. couch 110, and thereby the patient support surface, about pitch axis 12. Alternatively or additionally, the rotation system may be configured to tilt the couch 110 about roll axis 14. Alternatively or additionally, the rotation system may be configured to tilt the couch 110 about yaw axis 16. Moreover, the couch 110 may be configured to move laterally, e.g. along the axis indicated by reference sign 12, longitudinally, e.g. along the axis indicated by reference sign 14, and/or vertically, e.g. along the axis indicated by reference sign 16. The couch 110 may therefore have six degrees of freedom—three translational degrees of freedom and three rotational degrees of freedom.

Returning now to FIG. 1*a*, the treatment system 134 includes a radiation head 104 and a detection device 106 (also referred to as a radiation detector). The treatment system 134 may be, for example, a MV radiation treatment system.

The radiation head 104 and the detection device 106 are mounted opposite each other on the gantry 102, with a rotational axis of gantry 102 positioned between them. The radiation head 104 is a source of radiation, configured to generate a radiation beam 122 according to a treatment plan to deliver doses of radiation to a patient (or subject) supported by the couch 110. The radiation head 104 includes a beam shaping apparatus (for example a collimator and/or MLC) for shaping the radiation beam 122. The radiation head 104 provides a beam of therapeutic radiation which may, for example, be in the megavoltage (MV) range. The detection device 106 detects radiation produced by the radiation head 104, for example after it has passed through a patient or phantom on the couch 110.

The gantry 102 is configured to rotate the radiation head 104 and detection device 106 about the couch 110, to provide patient with a plurality of dosages of radiation according to the treatment plan.

The imaging system 136 comprises an imaging beam source 118 and an imaging panel 120. The imaging system may be, for example, a cone beam computed tomography (CBCT) system.

The imaging beam source 118 produces non-therapeutic radiation, for irradiating a patient or phantom on the couch 110. The imaging panel 120 is configured to detect radiation produced by the imaging beam source 118, producing signals indicative of the intensity of radiation incident on the imaging panel 120. In use, these signals are indicative of the intensity of radiation which has passed through the patient. These signals may be processed to form an image of the patient. This process may be described as the imaging system 136 and/or the imaging panel 120 capturing an image.

By capturing two-dimensional (2D) images at multiple angles around the patient, and combining them, it is possible to produce a 3D image of the patient, for example using tomographic reconstruction techniques.

The controller 140 may be programmed to control features of the apparatus 100 according to a radiotherapy treatment plan for irradiating a target tissue of a patient. A treatment plan may include information about a particular dose to be applied to a target tissue, as well as other parameters such as beam angles, dose-histogram-volume information, the number of radiation beams to be used during therapy, the dose per beam, and the like. The controller 140 is programmed to control various components of apparatus 100—such as gantry 102, radiation head 104, detection device 106 and couch 110—according to the predetermined treatment plan.

The controller 140 is configured to control the couch 110 via the one or more actuators 108 of the couch. For example, the controller 140 outputs control signals to the one or more actuators 108.

The radiotherapy apparatus 100 has an isocentre (also referred to as a rotational isocentre). In an ideal system, the isocentre is the point in space created by the intersection of the gantry rotation axis and the plane which contains the trajectory of the radiation emitted by the source. This point often serves as the geometric origin for the modelling of the radiation delivery in any treatment planning system and any patient imaging system.

The radiotherapy apparatus 100 is configured to perform at least one of a helical treatment or a multi-isocentre treatment, based on a corresponding treatment plan.

In a helical treatment, the radiotherapy apparatus is configured to rotate the gantry 102 supporting the radiation head 104 and to apply continuous radiation from the radiation head 104 as it rotates about the patient, whilst the patient is moved via translation of the couch 110. By moving the patient through the radiation plane as the radiation source 104 is rotated, the radiation beam sweeps out a helical shape from the patient's perspective. The pitch of the helix can be adjusted by varying the speed of movement of the couch 110. The helical treatment can start while the beam is aimed at a first anatomical location, for example at a particular vertebra of a patient's spine, and end while the beam is aimed at a second anatomical location, for example a different vertebra. Thus, radiation is applied to the segment of the spine located in between the two locations, as an elongate target region, as the gantry rotates.

In a multi-isocentre treatment, the radiotherapy apparatus is configured to treat multiple distinct anatomical locations. This technique is useful if a target (e.g. a lesion) has such a shape or length that it benefits from multi-isocentre treatment (e.g. if a target doesn't fit the physical characteristics of an MLC). This can be done by irradiating a first anatomical location, stopping the application of radiation and moving the couch 110, and then irradiating a second anatomical location which has been placed in the path of the beam due to movement of the couch 110.

FIGS. 2*a* and 2*b* show simplified schematic overhead views of the radiation head and the couch according to the invention.

In FIG. 2*a*, patient 171 is supported by the couch 110. The patient's spine is shown schematically as a box 220. The patient's spine 220 includes a first anatomical location L1 and a second anatomical location L2. The spine 220 and both anatomical locations L1, L2, are aligned along the gantry axis of rotation (represented by a dashed line), in accordance with a treatment plan for the patient. Although the first and second anatomical locations L1, L2 are illustrated and described in this example as being located on a patient's spine, it is to be understood that this is merely exemplary. The anatomical locations L1 and L2 may be in any region in or on the body, or indeed in or on a phantom as part of a quality assurance checking procedure.

In FIG. 2*a*, the couch 110 is positioned such that the radiation head 104 can deliver the beam 122 to the first anatomical location L1. It can be seen that the direction of the beam 122 is substantially perpendicular to the axis of rotation 10 (the z axis). In this example, the first anatomical location L1 is located at an isocentre of the radiotherapy apparatus, which is a target location where radiation will be delivered. It is noted that the positioning of the first anatomical location L1 at the isocentre is merely exemplary. In some embodiments, the first anatomical location L1 may be positioned at a point at which the MLC is configured to deliver a beam, which may be distinct from the isocentre.

A reference point P is illustrated on an edge of the couch 110.

FIG. 2*b* shows the couch 110 after being moved according to a vector V, as shown by the change in position of reference point P. The vector corresponds to a distance between the first anatomical location L1 and the second anatomical location L2. Here, the vector V defines a translation of the couch 110 along the z axis (the axis of rotation).

In the position shown in FIG. 2*b*, the couch 110 is positioned such that the radiation head 104 can deliver the beam 122 to the second anatomical location L2. In this example, the second anatomical location L2 is now located at the isocentre of the radiotherapy apparatus. That is, the couch 110 has been moved from the position shown in FIG. 2*a* to the position shown in FIG. 2*b*, in which the second anatomical location L2 is aligned with the isocentre of the radiotherapy apparatus.

In FIGS. 2*a* and 2*b*, the couch translates in a linear direction perpendicular to the gantry plane, and translated along the rotation axis of the gantry.

In the example shown in FIGS. 2*a* and 2*b*, since the first and second anatomical locations were aligned along the axis of rotation (z-axis), in accordance with the treatment plan, the correct dose can be delivered to each of the anatomical locations without deviating from the treatment plan.

FIGS. 3*a* and 3*b* show simplified schematic overhead views of the radiation head and the couch according to the invention. These figures illustrate how a deviation, e.g. angular deviation p, between the position of the patient 171 at the time of treatment relative to their planned position according to the treatment plan can result in a dose error.

FIG. 3*a* shows a scenario in which the patient's spine 220 is not entirely aligned with the rotation axis 10. As can be appreciated from the figure, first anatomical location L1 is located at a target location for the beam of therapeutic radiation (such as the rotational isocentre). However, a small local angular deviation p has been introduced during set-up, e.g. when the patient 171 is first positioned on the couch 110. In other words, the elongate axis of the patient's spine forms an angle β with respect to the rotational axis 10 of the gantry. Even if this angular deviation is small, after the couch has been moved along vector V according to a normal helical treatment plan (e.g. in a manner not in accordance with the present disclosure), the second anatomical location L2 does not fall optimally in the beam path and the intended target area for irradiation is no longer aligned with the rotational axis 10 of the apparatus.

As shown in FIG. 3*b*, as the radiation head 104 is rotated around the patient, the beam will be aligning with a location 301 which is translated from location L2, for example centred on the axis of rotation of the gantry. This can result in an dose error, where the dose distribution is translated away from the location L2, and instead the dose is delivered to erroneous location 301.

FIGS. 4*a* and 4*b* show simplified schematic overhead views of the radiation head and the couch according to the present disclosure. In this example, a vector V is used to move the couch 110, where vector V' is calculated based on a determined angular deviation of the patient 171 between a patient's position at the time of treatment and a predetermined patient position corresponding to a treatment plan. Although a deviation between a planned patient position and an actual patient position is described herein, this is merely exemplary. In some embodiments, a vector between the first anatomical location L1 and the second anatomical location L2 may be defined, and the angular deviation may be based on an angular deviation of the determined vector relative to the rotational axis of the gantry.

In some embodiments, the predetermined patient position corresponding to a treatment plan may correspond to a vector determined using one or more anatomical locations L1, L2. That is, the treatment plan may indicate or correspond to a position of the patient in which anatomical positions L1 and L2 are aligned or substantially aligned with a rotational axis of the gantry.

In FIG. 4*a*, an angular deviation p is shown, illustrating a deviation between a trajectory between two anatomical locations L1, L2 and a rotational axis 10 of the gantry, similarly to FIG. 3*a*. The deviation may be, for example, an angular deviation between a longitudinal axis of the patient 171 and the rotational axis of the gantry, or an angular deviation between a vector determined based on the locations of the anatomical locations L1 and L2 and the rotational axis of the gantry. In some embodiments, the angular deviation may comprise a deviation between a position of the patient 171 at the time of treatment and a predetermined patient position corresponding to a treatment plan. In FIG. 4*b*, the couch 110 has been moved according to vector V, e.g. in a translated manner in the x-z plane, and the couch 110 is thus positioned such that the radiation head 104 can deliver the beam to the second anatomical location L2. This reduces or minimises the error in dose distribution at location L2.

Although in FIGS. 3*a*, 3*b*, 4*a* and 4*b* illustrate examples with two anatomical locations L1 and L2, it is to be understood that this is merely exemplary. Any number of anatomical locations may be present, and a plurality of vectors may be used to move the couch 110 multiple times. For example, in a case where three anatomical locations L1, L2 and L3 are present (such as along a patient's spine), a first vector between L1 and L2 may be determined, and a second vector between L2 and L3 may be determined. After delivering radiation to the first anatomical location L1 (e.g. in accordance with a treatment plan), the couch 110 may be moved according to the first vector such that the second anatomical location L2 is aligned with the isocentre of the apparatus. After delivering radiation to the second anatomical location L2 (e.g. in accordance with a treatment plan), the couch 110 may then be moved according to the second vector, such that the third anatomical location L3 is aligned with the isocentre of the apparatus, and so on. The use of such multiple vectors may also be used in helical treatment, for example to treat elongate regions which are not purely linear, which are curved, or which are otherwise difficult to access.

Calculation of the vector V is described in more detail below.

As shown in FIG. 4*b*, as the radiation head 104 is rotated around the patient, the beam aligns with location L2 (for example as L2 has been moved to the isocentre of the apparatus). This reduces or minimises dose error. In cases where the deviation is due to a difference between a patient position at time of treatment and the patient position corresponding to a treatment plan, for example, the only error may be a small local angular error, as the beam is arriving at location L2 from a slightly different angle than envisaged in the treatment plan.

Although the isocentre has been referred to in the examples above, it will be appreciated that this is merely exemplary. The radiation beam can be directed to treat target locations which are offset from the isocentre.

FIGS. 5*a* and 5*b* show simplified schematic overhead views of the radiation head and the couch according to the invention. As shown in FIGS. 5*a* and 5*b*, a target region 230 may be elongate and/or have a shape which is not strictly linear. In the example shown, the target region 230 is curved. The target region 230 may have a plurality of anatomical locations, such as L1 and L2. That is, multiple anatomical locations such as L1 and L2 may be on the same target region 230.

FIGS. 5*c* and 5*d* illustrate a target region with a plurality of anatomical locations according to the invention. As shown in FIG. 5*c*, a target region 230 may have a substantially non-linear shape. In this example, the target region 230 is shown with three anatomical locations L1, L2 and L3. A first vector $V'_1$ may be determined based on L1 and L3, as shown, having a directional component $\beta_1$, The directional component $\beta_1$ may be an angular deviation between the vector $V'_1$ and the rotational axis of the gantry, indicated in FIG. 5*c* by the horizontal dotted line 10.

In some embodiments, radiation may be applied to the first anatomical location L1 and subsequently, the couch 110 may be moved according to vector $V'_1$ to align L3 with the isocentre of the apparatus (or with a point at which the beam is programmed to be delivered). That is, in some embodiments, radiation may be applied at discrete locations L1 and L3, without being applied during the movement of the couch 110. In other embodiments, however, radiation may be applied during the movement of the couch 110 from the first anatomical location L1 to the third anatomical location L3 along vector $V'_1$. The latter may be used to deliver helical treatment.

FIG. 5*d* shows the target region 230 after the couch 110 has been moved according to vector $V'_1$—that is, from an initial position in which the first anatomical location L1 is aligned with a point at which the apparatus is configured to deliver radiation (e.g. the isocentre), to a subsequent position in which the third anatomical location L3 is aligned with the point at which the apparatus is configured to deliver radiation (e.g. the isocentre). From the third anatomical location L3, the couch 110 may be moved according to vector $V'_2$, determined based on anatomical locations L3 and L2. The directional component $\beta_2$ of vector $V'_2$ may be an angular deviation between the vector $V'_2$ and the rotational axis of the gantry 10. Radiation may then be delivered to the second anatomical location L2, e.g. in accordance with a treatment plan. The calculation and use of multiple vectors will be further described under the heading "Multiple Vectors".

As described above, in some embodiments, a plurality of anatomical locations may be distinctly treated, e.g. without radiation being applied therebetween. In other embodiments, however, the first anatomical location L1 may be the starting point of a helical treatment, and the second anatomical location L2 may be an ending point, or in some cases an intermediate point, for the helical treatment.

In this case, radiation is applied as the couch is moved along vector V', allowing a target region extending between L1 and L2 (e.g. along the spine) to be irradiated. In some embodiments with more than two anatomical positions, helical treatment may be applied starting from the first anatomical location L1 to the second anatomical location L2 along a first vector V, and then from the second anatomical location L2 to a third anatomical location L3 along a second vector (and so on).

By moving the couch 110 according to vector V, it is possible to carry out a planned treatment without having to reposition the patient on the couch itself, e.g. once the dose translation error is too big, and without having to have a couch capable of rotating, and/or to plan and carry out a treatment which reduces the amount of repositioning of the patient, whilst improving the accuracy and therefore efficacy of the beam delivery. Moreover, the treatment of target regions with non-linear shapes may be simplified and provided more efficiently and reliably.

FIG. 6 is a flowchart setting out a method for controlling a radiotherapy apparatus to compensate for angular deviation(s) during a radiotherapy treatment, such as a helical treatment.

In step 610, a first anatomical location L1 of a patient is obtained.

In step 620, a second anatomical location L2 of the patient is obtained. Steps 610 and 620 may be performed in any order or simultaneously. In some embodiments, the first anatomical location L1 and the second anatomical location L2 may be on the same target region, such as on a single elongate target region. In other embodiments, the first anatomical location L1 and the second anatomical location L2 may be on different target regions.

In some embodiments, obtaining the first and/or second anatomical position of the patient may comprise receiving image data for the patient and identifying the first and/or second anatomical position L1, L2 using the received image data. The image data may be for a patient on the subject support surface, e.g. at a time of treatment (or immediately prior to treatment). The image data may provide an indication of the positioning of the patient on the subject support surface. This image data may be 3D image data, acquired using, for example, cone beam computed tomography (CBCT), Computed Tomography (CT) or magnetic resonance imaging (MRI) in the case of an MRI-linac. The image data may, in some embodiments, be obtained using an imaging system of the radiotherapy apparatus. The image data may provide visualisation of patient anatomy, preferably including a first anatomical location L1 and a second anatomical location L2 of the patient.

In some embodiments, the image data is registered (e.g. co-registered) with reference image data in order to determine a difference in the alignment of the image data relative to the reference image data. This may involve geometrically aligning the first image data with the reference data in order to determine the angular deviation therebetween, e.g. automatically. A computer may used for this purpose. This angular deviation may be taken from a reference axis—for example an angle β from the axis of rotation of the radiotherapy apparatus. The angular deviation may define deviations in multiple dimensions—for example it may comprise at least one of three angular error values around three spatial axes, e.g. defining roll, pitch and yaw.

The reference image data may have been acquired in a scan prior to the radiotherapy treatment, and prior to obtaining the image data. The scan may be done using, for example, a computerised tomography (CT) scan, in which case the reference image data comprises a planning CT dataset. The reference image data may be associated with a treatment plan for the patient.

The first and second anatomical locations L1, L2 of the patient may be identified in a coordinate system of the radiotherapy apparatus. The first anatomical location L1 may be a particular anatomical feature—for example all or part of a tumour, and may be a starting location of a helical treatment. The second anatomical location L2 may be a particular anatomical feature—for example all or part of a tumour, and may be an ending location of a helical treatment.

In some embodiments, further anatomical locations L3, L4 . . . Ln can be identified. Obtaining, e.g. identifying, anatomical locations can be done using known methods—for example during treatment planning one or more target volumes can be identified, e.g. using contouring delineation, and the anatomical locations may correspond to one or more of the identified target volumes. In one example, each anatomical location is a centre of a target volume.

In step 630, a vector V is determined using the first anatomical location L1 and the second anatomical location L2. A directional component of the vector V may be an angular deviation from the rotational axis of the gantry. The vector may account for the distance between the locations L1, L2, and their relative positions in the coordinate system of the radiotherapy apparatus. It may be calculated using a measurement of angular deviation from a reference axis—for example an angle β from the axis of rotation of the gantry. In some embodiments, the vector V may be a vector from the first anatomical location L1 to the second anatomical location L2.

In a simplified example, if the distance between L1 and L2 is a first distance d, and the angular deviation from the z-axis (e.g. the rotational axis of the gantry) is p in the x-z plane, then the x and z components of the vector V' are as follows:

X component=d sin β

Z component=d cos β

It will be appreciated that the vector V may have components in all three spatial dimensions x, y, z.

At step 640, the radiation head 104 is controlled to apply radiation to the first anatomical location L1 at a first time T1. This step is generally performed in accordance with the treatment plan—for example starting a helical treatment defined by the plan. The treatment plan preferably defines a gantry angle, dose, and collimator setting for each anatomical location L1, L2 . . . Ln, thereby defining what dose is to be delivered for a certain angle.

Next, at step 650, the subject support surface is moved based on the vector V. In some embodiments, radiation may be applied during movement of the couch. For a helical treatment, the radiation head 104 is controlled to rotate around the patient and apply radiation in a radiation plane as the subject support surface is moved through the radiation plane based on vector V'. This results in a radiation dose being delivered to an elongate target region between anatomical locations L1 and L2. In some cases, the movement of the subject support surface along the vector V may be included in a treatment plan. In other cases, however, movement of the subject support surface along the vector V may be a modification to the treatment plan, for example if there is a deviation between the patient positioning at time of treatment and the predetermined patient positioning associated with the treatment plan. In such cases, if the vector V has an angular deviation based on a difference between the actual patient position (at time of treatment) and the planned patient position, the dose may be delivered differently than prescribed in the treatment plan in order to compensate for the difference (the method is therefore referred to as "soft-adaptive"). This is because the treatment plan to be delivered by the machine assumes an ideal alignment of the patient and thus assumes movement of the couch 110 such as a translation along the axis of rotation (z axis), with no x component.

At step 660, the radiation head 104 is controlled to apply radiation to the second anatomical location L2 at time T2. This step is also generally performed in accordance with the treatment plan—for example L2 may mark the end of the helical treatment.

Due to the movement of the couch 110 based on the vector V', translational errors in dose distribution are reduced. The only errors which are uncompensated are small local angular errors—since at each location the beam is arriving with a slightly different angle than envisaged in the treatment plan. However, the effect of these local angular error is very small and acceptable for most treatments—particularly for a helical treatment, the effect on overall dose distribution is minor. In some implementations, local angular errors can be controlled via a recalculation of the dose to be delivered, taking the vector V into account.

In some implementations, before delivery, the soft adaptive plan can be accepted either by a user or automatically via pre-defined constraints. If the plan cannot be accepted, a user either may have to realign the patient or fully replan the treatment that is to be delivered—using full adaptive technology.

In some embodiments, radiation may be applied during step 650, e.g. during movement of the subject support surface based on vector V', for example to provide a helical treatment treating an elongate region. In other embodiments, radiation may be applied discretely, such as to irradiate separate and distinct target regions.

Multiple Vectors

The vector V between locations L1 and L2 may be a 'best fit' vector. In some embodiments, the angular deviation between a patient position at time of treatment and a predetermined patient position associated with a treatment plan may stem from non-rigid shifts in patient anatomy. In embodiments where the deviation comprises large non-rigid shifts, the resulting 'best fit' vector may be divided into a number of segments, e.g. a series of connecting vectors, in order to remain substantially equivalent to the deviation.

In some examples, when image data (e.g. taken at or immediately preceding treatment) is registered (e.g. co-registered) with reference image data, the registration can be divided into segments, with an angular deviation and associated vector being determined for each segment. This can result in a series of connected vectors. In some cases, each pixel/voxel of the image data and the reference image data is registered, and an associated vector is defined for each pixel/voxel. Alternatively or additionally, segments made up of multiple pixels/voxels can be registered and an associated vector is determined for each segment.

The couch can be controlled to move in accordance with a sequence of vectors—e.g. multiple connected vectors determined from multiple registered segments.

In some embodiments, the method outlined above can further comprise obtaining (e.g. identifying) a third anatomical location L3 of the patient in the coordinate system of the radiotherapy apparatus. In such embodiments, steps 630 to 660 are repeated, using L2 and L3 instead of L1 and L2. This allows compensation for the angular deviation between a vector determined using the second and third anatomical locations and the rotational axis of the gantry, particularly where the angular deviation is different than between L1 and L2 (e.g. when the directional component of the first vector determined using L1 and L2 differs from the directional component of the second vector determined using L2 and L3). This can be repeated for as many locations as desired L1, L2 . . . Ln.

Using such multiple vectors is useful to perform helical treatments where target regions or parts of target regions have different angular deviations (for example where the target region is subject to non-rigid deformations or where the shape of the target region is non-linear). Using multiple vectors in this manner may also be useful to perform non-helical treatment to a plurality of target regions which are not all aligned.

In some examples, the beam applied to the target region is shaped by the beam shaping apparatus (e.g. MLC), where the shape defined by the beam shaping apparatus varies depending on the alignment of the beam and the target region. For instance, an MLC can define an aperture of a different shape when the beam angle changes, in order to match the shape of the target region at the given beam angle. In some examples, a target region which is offset from the rotational isocentre can be irradiated by controlling the beam shaping apparatus to direct the radiation beam to the target location away from the rotational isocentre, while blocking radiation from passing to the rotational isocentre. The above-described methods can be used to account for any angular deviations of all or part of a target region which is offset from the rotational isocentre. In some examples, by using beam shaping depending on the alignment of the beam with the target region, and by moving the couch according to multiple vectors determined from one or more angular deviations, a curved target region can be treated in a more accurate way.

Modifying the movement vector for the couch provides an effective way of improving accuracy of radiotherapy treatment, while reducing treatment plan modification (for example, avoiding the need to modify MLC leaf positions).

The above implementations have been described by way of example only, and the described implementations and arrangements are to be considered in all respects only as illustrative and not restrictive. It will be appreciated that variations of the described implementations and arrangements may be made without departing from the scope of the invention.

The labels (e.g. x, y, z) used for axes, directions, etc. are arbitrary and any suitable label can be used.

The movement of the couch in a translational manner may be done in a continuous motion, such that the beam is delivered continuously along the dashed line between the first and second anatomical locations. Alternatively, discrete translational movements of the couch may take place, with a dose of radiation applied at a particular angle after/during each discrete movement. For example, beam delivery may occur only at L1 and L2. This may be suitable for treating two or more discrete target regions, for example a plurality of closely-spaced tumours.

In some examples, the method of control involves controlling movement of the subject support surface during treatment delivery based on vector V, such that the first treatment location, L1, is intersected by the beam at time T1, and the second treatment location, L2, is intersected by the beam at time T2. The method may further comprising determining the vector based on yaw and pitch components of the angular deviation.

Instead of steps 640, 650 and 660 being carried out as described above, the method may instead comprise the output of control instructions configured to control the radiotherapy apparatus to: apply radiation to the first anatomical location L1 at time T1; move the subject support surface based on the vector; and apply radiation to the second anatomical location L2 at time T2.

In step 650 the couch may be moved based on the determined angular deviation. The movement can be translation, rotation, or a combination of both.

The couch may have one or more rotational degrees of freedom. The controller may be configured to rotate the couch based on a determined angular deviation, in order to reduce or eliminate the angular deviation. For example, the controller can cause radiation to be applied to the first anatomical location L1 at time T1, move the subject support surface based on the angular deviation, wherein the movement comprises a rotation based on the angular deviation, and cause radiation to be applied to the second anatomical location L2 at time T2.

In some examples, the controller may be configured to rotate the couch based on the angular deviation, and to calculate the one or more vectors based on the angular deviation and taking into account the rotation. In some examples, the rotation of the couch in the one or more rotational degrees of freedom may be limited to a maximum number of degrees (e.g. plus or minus 5 degrees) and therefore the controller can account for determined angular deviation through a combination of rotation of the couch (up to the maximum rotation) and generation of one or more vectors used in movement of the couch.

The controller is a computing device, computer, processor, or other processing apparatus. The controller may be formed by several discrete processors. The controller can be provided by multiple separate controllers (separate in hardware and/or software), and may include distributed components. This can include physical and functional components in different elements of the system.

The controller may perform functions or operations such as treatment planning, treatment execution, image acquisition, image processing, motion tracking, motion management, and/or other tasks involved in a radiotherapy process.

Software components of the controller 140 may include operation device software, application software, etc. These software components may have in-built algorithms or processes for extracting information on target motion from a suitable form of motion data, and may use further algorithms or processes to determine control instructions based on this information.

FIG. 7 is a block diagram of one implementation of a controller such as a computing device 700 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a secondary memory (e.g., a data storage device 718), which communicate with each other via a bus 730.

Processing device 702 represents one or more general-purpose processors such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 702 is configured to execute the processing logic (instructions 722) for performing the operations and steps discussed herein.

The computing device 700 may further include a network interface device 708. The computing device 700 also may include a video display unit 710 (e.g., a liquid crystal display (LCD) or a cathode ray tube (CRT)), an alphanumeric input device 712 (e.g., a keyboard or touchscreen), a cursor control device 714 (e.g., a mouse or touchscreen), and an audio device 716 (e.g., a speaker).

The data storage device 718 may include one or more machine-readable storage media (or more specifically one or more non-transitory computer-readable storage media) 728 on which is stored one or more sets of instructions 722 embodying any one or more of the methodologies or functions described herein. The instructions 722 may also reside, completely or at least partially, within the main memory 704 and/or within the processing device 702 during execution thereof by the computer system 700, the main memory 704 and the processing device 702 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

The invention claimed is:

1. A radiotherapy apparatus comprising:
a radiation source coupled to a rotatable gantry;
a movable subject support surface; and
a controller configured to:
obtain a first anatomical location of a patient and a second anatomical location of the patient;
determine a vector using the first anatomical location and the second anatomical location, a directional component of the vector being an angular deviation from a rotational axis of the rotatable gantry;
apply radiation from the radiation source to the first anatomical location at a first time;
move the movable subject support surface relative to the rotatable gantry based on the angular deviation;
apply radiation from the radiation source to the second anatomical location at a second time; and
apply radiation according to a helical treatment, wherein the radiation applied according to the helical treatment is applied during the movement of the movable subject support surface and during rotation of the rotatable gantry.

2. The radiotherapy apparatus of claim 1, wherein the controller is configured to:
obtain the first anatomical location and the second anatomical location by receiving image data and identifying the first anatomical location and the second anatomical location using the received image data.

3. The radiotherapy apparatus of claim 2, wherein the controller is configured to:
determine the vector by registering the image data with reference image data, wherein the angular deviation is determined based on a difference in alignment between the image data and the reference image data.

4. The radiotherapy apparatus of claim 2, comprising:
an imaging system configured to generate image data, and wherein receiving the image data comprises receiving the image data from the imaging system.

5. The radiotherapy apparatus of claim 1, wherein the controller is configured to:

apply radiation to a target region between the first anatomical location and the second anatomical location as the movable subject support surface is moved.

6. The radiotherapy apparatus of claim 1, wherein the controller is configured to:

apply radiation according to a treatment plan.

7. The radiotherapy apparatus of claim 1, wherein the helical treatment is applied from the first anatomical location to the second anatomical location, and wherein movement of the movable subject support surface and rotation of the rotatable gantry occur concurrently during the helical treatment.

8. The radiotherapy apparatus of claim 1, wherein the first anatomical location and the second anatomical location are locations on a single target.

9. The radiotherapy apparatus of claim 1, wherein the first anatomical location corresponds to a position on a first target, and wherein the second anatomical location corresponds to a position on a second target, distinct from the first target.

10. The radiotherapy apparatus of claim 1, wherein the controller is further configured to:

obtain a third anatomical location of the patient;

determine a second vector using the second anatomical location and the third anatomical location, wherein a directional component of the second vector is a second angular deviation from the rotational axis of the rotatable gantry;

move the movable subject support surface relative to the rotatable gantry based on the second angular deviation; and apply radiation from the radiation source to the third anatomical location at a third time.

11. The radiotherapy apparatus of claim 1, further comprising:

a beam shaping apparatus configured to shape a beam of radiation, wherein radiation from the radiation source is applied as a beam shaped by the beam shaping apparatus, and wherein the controller is configured to control the beam shaping apparatus to shape the beam in accordance with a treatment plan and/or an alignment of the beam and a target to which radiation is being applied.

12. The radiotherapy apparatus of claim 1, wherein the controller is configured to move the movable subject support surface by translating the movable subject support surface in at least two spatial dimensions.

13. The radiotherapy apparatus of claim 1, wherein the angular deviation comprises at least one angular error value in at least one dimension.

14. A method for controlling a radiotherapy apparatus comprising a radiation source coupled to a rotatable gantry and movable subject support surface, the method comprising:

obtaining a first anatomical location of a patient and a second anatomical location of the patient;

determining a vector using the first anatomical location of the patient and the second anatomical location of the patient, a directional component of the vector being an angular deviation from a rotational axis of the rotatable gantry; and outputting control instructions configured to control the radiotherapy apparatus to:

apply radiation from the radiation source to the first anatomical location at a first time;

move the movable subject support surface relative to the rotatable gantry based on the angular deviation; and apply radiation from the radiation source to the second anatomical location at a time, wherein outputting control instructions configured to control the radiotherapy apparatus to move the movable subject support surface comprises:

outputting control instructions configured to control the radiotherapy apparatus to apply radiation to a target region between the first anatomical location and the second anatomical location as the movable subject support surface is moved.

15. The method of claim 14, wherein obtaining the first anatomical location and the second anatomical location comprises receiving image data and identifying the first anatomical location and the second anatomical location using the received image data.

16. The method of claim 15, wherein determining the vector comprises registering the image data with reference image data, and determining the angular deviation based on a difference in alignment between the image data and the reference image data.

17. The method of claim 15, wherein receiving the image data comprises generating the image data using an imaging system of the radiotherapy apparatus and receiving the image data from the imaging system.

18. The method of claim 14, further comprising:

outputting control instructions configured to control the radiotherapy apparatus to apply radiation according to a treatment plan.

19. The method of claim 14, further comprising:

outputting control instructions configured to control the radiotherapy apparatus to apply radiation according to a helical treatment in which radiation is applied during movement of the movable subject support surface and during rotation of the rotatable gantry.

20. The method of claim 19, wherein outputting control instructions configured to control the radiotherapy apparatus to apply radiation according to a helical treatment comprises:

outputting control instructions configured to control the radiotherapy apparatus to apply radiation according to a helical treatment from the first anatomical location to the second anatomical location.

21. The method of claim 14, wherein the first anatomical location and the second anatomical location are locations on a single target.

22. The method of claim 14, wherein the first anatomical location corresponds to a position on a first target, and wherein the second anatomical location corresponds to a position on a second target, distinct from the first target.

23. The method of claim 14, further comprising:

obtaining a third anatomical location of the patient;

determining a second vector using the second anatomical location and the third anatomical location, wherein a directional component of the second vector is a second angular deviation from the rotational axis of the rotatable gantry; and outputting control instructions configured to control the radiotherapy apparatus to:

move the movable subject support surface relative to the rotatable gantry based on the second angular deviation; and apply radiation from the radiation source to the third anatomical location at a third time.

24. The method of claim 14, further comprising:
outputting control instructions configured to control the radiotherapy apparatus to apply radiation as a beam shaped by a beam shaping apparatus, and to shape the beam in accordance with at least one of a treatment plan or an alignment of the beam and a target to which the radiation is being applied.

25. The method of claim 14, further comprising:
outputting control instructions configured to control the radiotherapy apparatus to move the movable subject support surface by translating the movable subject support surface in at least two spatial dimensions.

26. The method of claim 14, wherein the angular deviation comprises at least one angular error value in at least one dimension.

27. A non-transitory computer readable medium comprising computer-executable instructions which, when performed by one or more processors of a computer device, cause the one or more processors to:
control a radiotherapy apparatus comprising a radiation source coupled to a rotatable gantry and a movable subject support surface, wherein to control the radiotherapy apparatus, the computer-executable instructions cause the one or more processors to:
obtain a first anatomical location of a patient and a second anatomical location of the patient;
determine a vector using the first anatomical location of the patient and the second anatomical location of the patient, a directional component of the vector being an angular deviation from a rotational axis of the rotatable gantry; and
output control instructions configured to control the radiotherapy apparatus to:
apply radiation from the radiation source to the first anatomical location at a first time;
move the movable subject support surface relative to the rotatable gantry based on the angular deviation;
apply radiation from the radiation source to the second anatomical location at a second time; and
apply radiation according to a helical treatment, wherein the radiation applied according to the helical treatment is applied during the movement of the movable subject support surface and during rotation of the rotatable gantry.

* * * * *